(12) United States Patent
Kuslich et al.

(10) Patent No.: US 7,025,771 B2
(45) Date of Patent: Apr. 11, 2006

(54) TOOL TO DIRECT BONE REPLACEMENT MATERIAL

(75) Inventors: Stephen D. Kuslich, Stillwater, MN (US); Francis Peterson, Prescott, WI (US); James W. Ahern, Hopkins, MN (US)

(73) Assignee: Spineology, Inc., Stillwater, MN (US)

( * ) Notice: Subject to any disclaimer, the term of this patent is extended or adjusted under 35 U.S.C. 154(b) by 519 days.

(21) Appl. No.: 09/738,726

(22) Filed: Dec. 15, 2000

(65) Prior Publication Data

US 2002/0010472 A1 Jan. 24, 2002

Related U.S. Application Data

(63) Continuation-in-part of application No. 09/608,079, filed on Jun. 30, 2000, now abandoned.

(51) Int. Cl.
*A61B 17/58* (2006.01)
*A61B 17/60* (2006.01)
*A61F 2/00* (2006.01)
*A61F 2/32* (2006.01)
*A61F 2/34* (2006.01)

(52) U.S. Cl. .............................. 606/93; 606/53; 606/92; 606/94

(58) Field of Classification Search ............... 606/92, 606/93, 53, 94; 604/59, 60, 62, 63, 64; 623/17.11, 623/71.16; 222/200, 204
See application file for complete search history.

(56) References Cited

U.S. PATENT DOCUMENTS

| | | | |
|---|---|---|---|
| 4,349,921 A | 9/1982 | Kuntz | 3/1 |
| 4,399,814 A * | 8/1983 | Pratt et al. | 606/94 |
| 4,466,435 A * | 8/1984 | Murray | 606/94 |
| 4,488,549 A * | 12/1984 | Lee et al. | 606/94 |
| 4,501,269 A | 2/1985 | Bagby | 128/92 |
| 4,576,152 A * | 3/1986 | Muller et al. | 606/93 |
| 4,625,722 A * | 12/1986 | Murray | 606/95 |
| 4,655,749 A * | 4/1987 | Fischione | 604/97.03 |
| 4,751,921 A * | 6/1988 | Park | 606/93 |
| 4,815,454 A * | 3/1989 | Dozier, Jr. | 606/94 |
| 4,834,757 A | 5/1989 | Brantigan | 623/17 |
| 4,865,604 A | 9/1989 | Rogozinski | 623/18 |
| 5,015,255 A | 5/1991 | Kuslich | 623/17 |
| 5,071,040 A * | 12/1991 | Laptewicz, Jr. | 222/235 |
| 5,181,918 A * | 1/1993 | Brandhorst et al. | 606/92 |
| 5,303,718 A | 4/1994 | Krajicek | 128/897 |
| 5,324,273 A * | 6/1994 | Discko, Jr. | 604/240 |
| 5,431,654 A * | 7/1995 | Nic | 606/92 |
| 5,443,514 A | 8/1995 | Steffee | 623/17 |
| 5,501,687 A * | 3/1996 | Willert et al. | 606/94 |

(Continued)

FOREIGN PATENT DOCUMENTS

| | | |
|---|---|---|
| DE | A61F2/46 | 11/1990 |
| DE | 29908794 U1 | 7/1999 |
| GB | 2262238 A | 12/1992 |
| WO | 99/08616 | 2/1999 |
| WO | 00/28907 | 5/2000 |

OTHER PUBLICATIONS

U.S. Appl. No. 09/608,079, filed Jun. 30, 2000, Kulisch et al.

*Primary Examiner*—Henry Bennett
*Assistant Examiner*—Nihir Patel
(74) *Attorney, Agent, or Firm*—Patterson, Thuente, Skaar & Christensen, P.A.

(57) ABSTRACT

A fill tool for directing bone replacement material into an expandable bag within a reamed out disc includes a deflector at its distal end which deflects the flow of such material to a one or more side openings at the distal end of the fill tool. This allows the tool to be used without being ejected when filling the bag under pressure and greatly increases the distraction forces possible when filling the bag.

16 Claims, 13 Drawing Sheets

U.S. PATENT DOCUMENTS

| | | | | |
|---|---|---|---|---|
| 5,549,679 A | | 8/1996 | Kuslich | 623/17 |
| 5,571,189 A | | 11/1996 | Kuslich | 623/17 |
| 5,577,517 A | * | 11/1996 | Bonutti | 128/898 |
| 5,697,932 A | * | 12/1997 | Smith et al. | 606/80 |
| 5,702,454 A | * | 12/1997 | Baumgartner | 128/898 |
| 5,718,707 A | * | 2/1998 | Mikhail | 606/94 |
| 5,782,919 A | | 7/1998 | Zdeblick et al. | 623/17 |
| 5,824,087 A | * | 10/1998 | Aspden et al. | 606/94 |
| 5,842,786 A | * | 12/1998 | Solomon | 366/139 |
| 5,997,581 A | * | 12/1999 | Khalili | 623/23.48 |
| 5,997,582 A | | 12/1999 | Weiss | 623/23 |
| 6,004,325 A | * | 12/1999 | Vargas, III | 606/94 |
| 6,019,765 A | * | 2/2000 | Thornhill et al. | 606/94 |
| 6,022,376 A | | 2/2000 | Assell et al. | 623/17 |
| 6,447,514 B1 | * | 9/2002 | Stalcup et al. | 606/63 |
| 6,554,803 B1 | * | 4/2003 | Ashman | 604/218 |
| 6,599,293 B1 | * | 7/2003 | Tague et al. | 606/94 |
| 6,620,162 B1 | * | 9/2003 | Kuslich et al. | 606/53 |
| 6,620,169 B1 | * | 9/2003 | Peterson et al. | 606/93 |
| 6,626,912 B1 | * | 9/2003 | Speitling | 606/92 |
| 6,645,213 B1 | * | 11/2003 | Sand et al. | 606/92 |
| 6,676,664 B1 | * | 1/2004 | Al-Assir | 606/94 |
| 2004/0215201 A1 | * | 10/2004 | Lieberman | 606/93 |

* cited by examiner

TOOL TO DIRECT BONE REPLACEMENT MATERIAL

CROSS-REFERENCE TO RELATED APPLICATIONS

This application is a continuation-in-part (CIP) of Ser. No. 09/608,079 filed Jun. 30, 2000 now abandoned.

STATEMENT REGARDING FEDERALLY SPONSORED RESEARCH OR DEVELOPMENT

Not Applicable.

BACKGROUND OF THE INVENTION

This invention relates to a tool for use injecting bone replacement material into a cavity within a bone, especially when the cavity includes a bag which is to be inflated within the cavity.

U.S. Pat. No. 5,549,679 issued Aug. 20, 1996 and U.S. Pat. No. 5,571,189 which issued Nov. 5, 1996 disclose an expandable fabric bag and method for stabilizing a spinal motion segment. In those patents, a damaged disc is reamed out and an expandable fabric bag is inserted into the cavity thus formed. Bone graft material is then inserted into the bag to fill and expand the bag such that the filled bag will take the place of the reamed out disc. Over time, the material within the bag will cause stabilization by either fibrous or bony fusion or a combination of these between the adjacent vertebrae. The bag filling is through an opening which is closed off after filling.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

BRIEF SUMMARY OF THE INVENTION

The invention provides a tool which dramatically increases the distraction forces within an expandable fabric bag held within a reamed out disc. Distraction consists of a force that is perpendicular to the long axis of the injection tube, thereby producing distraction or increased separation distance between the bony structures that are perpendicular to the long axis of the injection tube. This allows the spacing between the vertebrae to be adjusted by inflating the bag as desired. The tool may be used in connection with any surgical application in which graft material is to be deployed and is not limited to use in connection with discs or where bags are required.

BRIEF DESCRIPTION OF THE DRAWINGS

A detailed description of the invention is hereafter described with specific reference being made to the drawings in which.

DETAILED DESCRIPTION OF THE INVENTION

Figure 4:
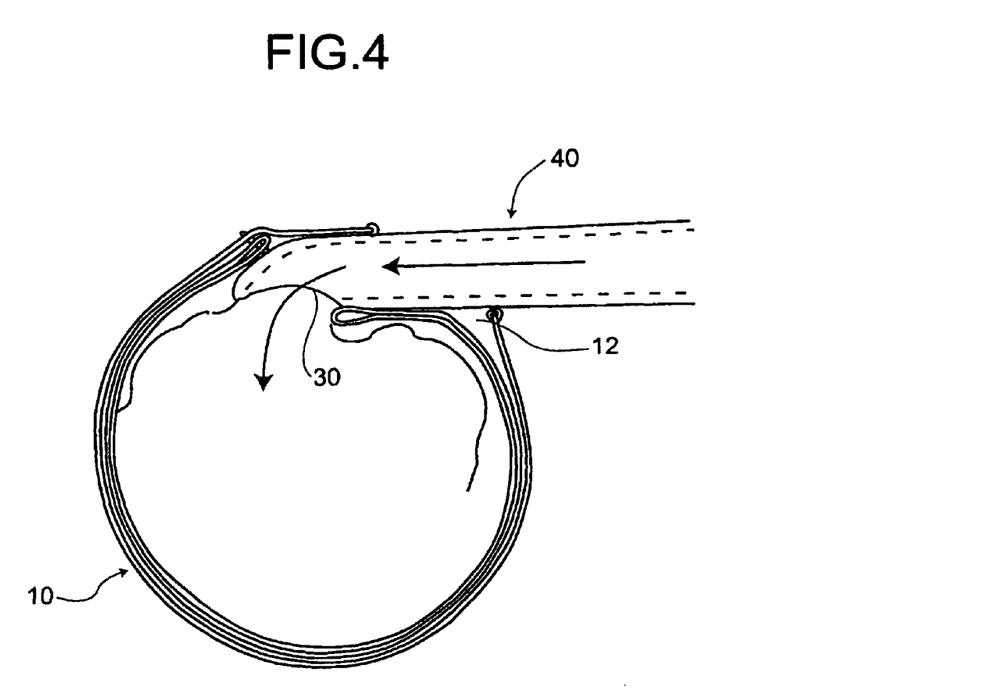
FIG. 4 is a cross-sectional view of a bag to be filled showing the filling tool inserted into the bag opening.

U.S. Pat. Nos. 5,571,189 and 5,549,679 are incorporated herein by reference. They show an expandable fabric bag which is to be inflated within a reamed out disc space by introduction of bone replacement material through the bag opening. As shown in FIG. 4, bag 10 of the patents is a fabric bag having an opening 12. The opening 12 may be closed off by any number of methods. It has been found that insertion of the bone graft material into the bag may result in low distraction forces and may allow the fill tube to be blown back out of the bag opening when fill pressure is increased.

The bone replacement material might be one or more of the following, or any other biocompatible material judged to have the desired physiologic response:

A) Morselized bone graft, cortical, cancellous, or corticocancellous, including autograft, allograft, or xenograft.

B) Any bone graft substitute or combination of bone graft substitutes, or combinations of bone graft and bone graft substitutes, or bone inducing substances, including but not limited to:
Hydroxyapatite
Bone morphogenic protein
Calcified or decalcified bone derivative C) Bone cements, such as ceramic and polymethylmethacrylate bone cements.

Figure 1:
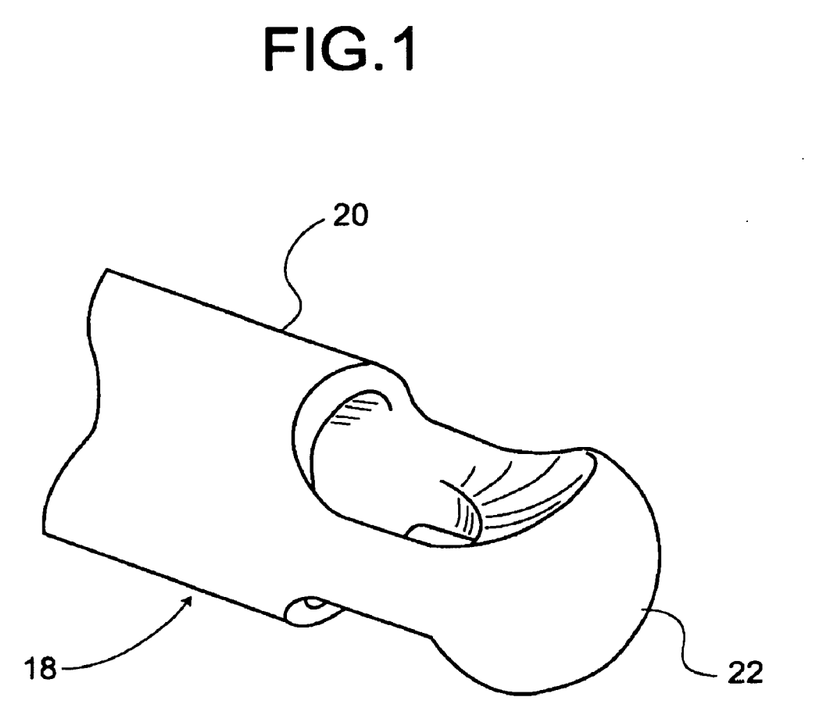
FIG. 1 is a perspective view of a distal end of a filling tool of the invention.
Figure 2:
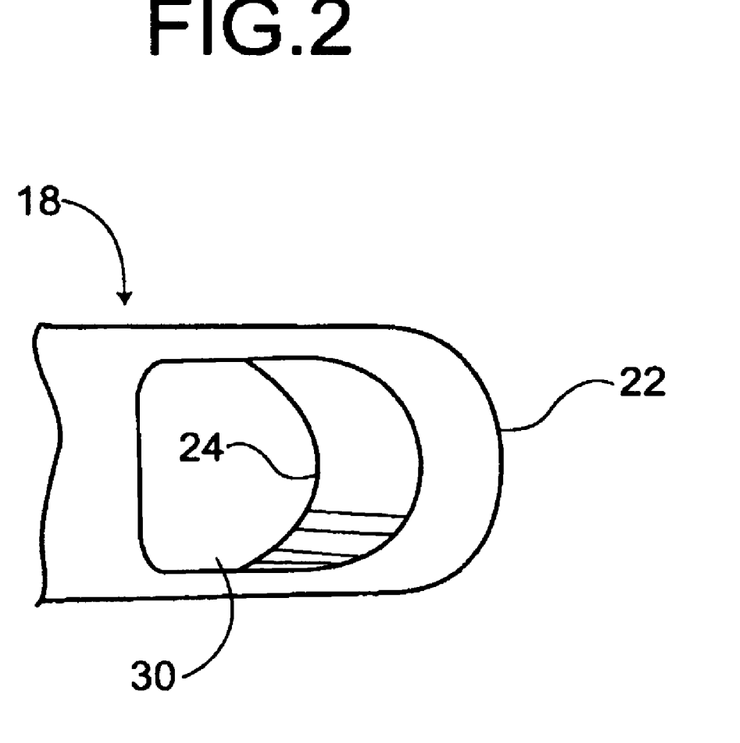
FIG. 2 is a side elevational view of the distal end of the tool of FIG. 1.
Figure 3:
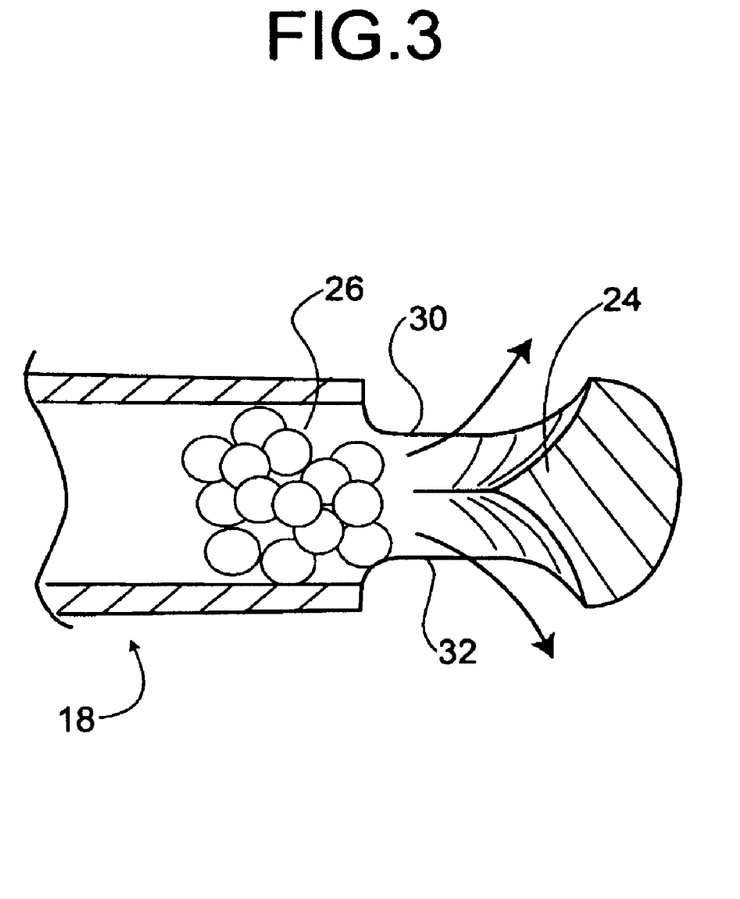
FIG. 3 is a cross-sectional view of the distal end of the filling tool of the invention showing bone material therewithin.

The inventive fill tool 18 of FIGS. 1–4 involves an elongated hollow tube 20 having a proximal end which is attached to a source of bone replacement material under pressure and a distal end 22 which includes the inventive features. As seen, the distal end 22 includes a deflector 24 which deflects flow of bone replacement material 26 out the side openings 30, 32 at an angle. One or more side openings 30, 32 may be present. The deflector 24 as shown in FIG. 3 includes two side openings 30, 32 and the deflector is basically a tapered wedge which diverts flow outwardly to both sides. If only a single side opening is present, the deflector would deflect all flow to that side opening.

As shown in FIG. 4, a single side opening 30 allows deflection of the bone replacement material into the expandable fabric bag 10 at an angle relative to the longitudinal axis of the filling tool such that internal forces building up within the bag do not cause the tool 18 to be ejected out along its longitudinal axis. Rather, any forces inside the bag are exerted back on the sides of the tool 18 against the side walls of the bag, preventing ejection of the tool 18 and allowing more pressure to be applied within the bag 10.

The forces during filling provided by the device are perpendicular to the axis of the tube to stop tear through, to prevent the tube from being pushed out during filling, to direct the flow to get the distraction desired and to reduce the overall forces required. A straight tube with an open end has no distraction forces perpendicular to the tube and merely lays a long column of replacement material that needs to buckle before more material can be extruded from the tube. The inventive device breaks up the column of replacement material in the tube by cantilever forces. A straight tube with an open end creates a rigid bar of replacement material that can break a containment bag or damage body structures they press against or cause the tube to be ejected from the neck of the bag or body cavity opening.

Figure 5:
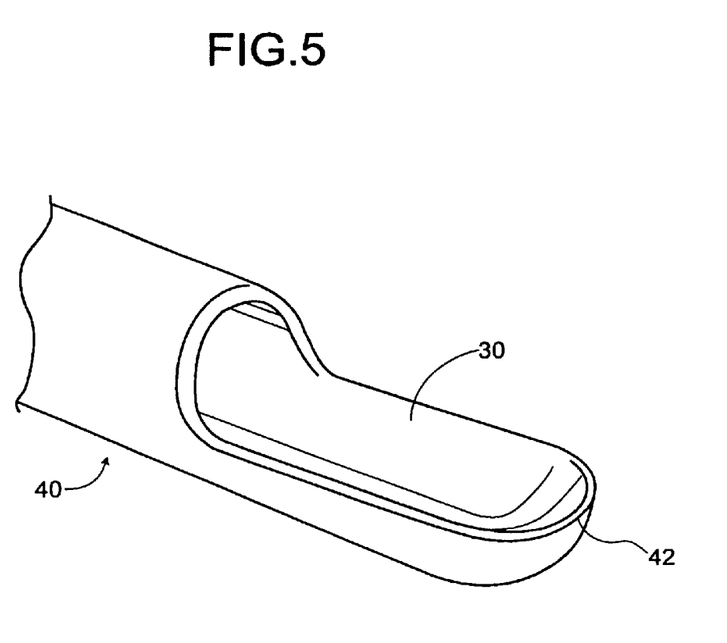
FIG. 5 is a perspective view of a distal end of an alternate filling tool of the invention.
Figure 6:
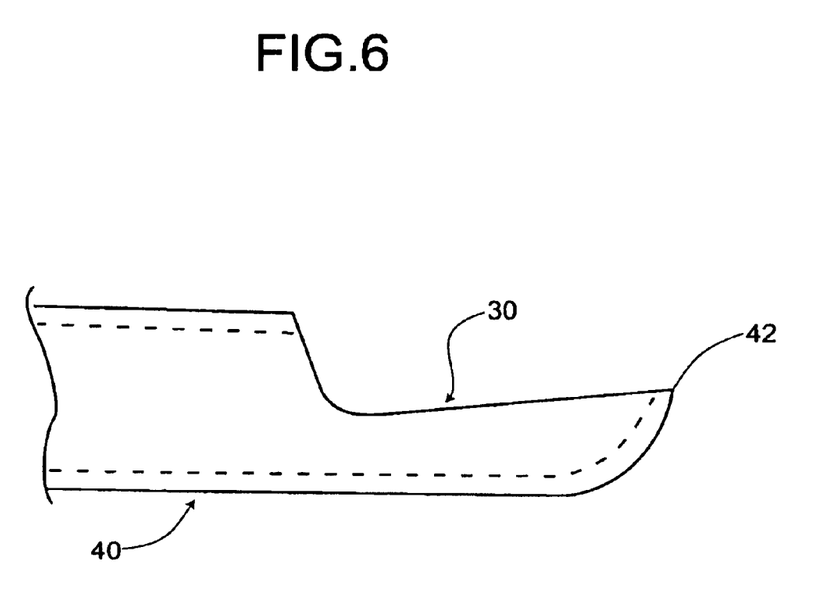
FIG. 6 is a side elevational view of the distal end of the tool of FIG. 5.
Figure 7:
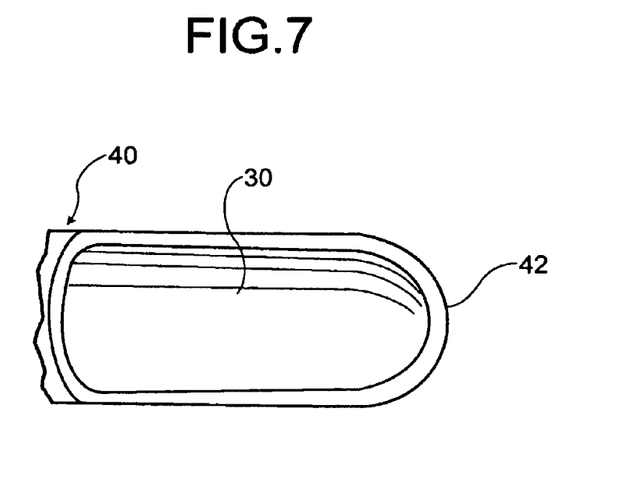
FIG. 7 is a top view of the opening at the distal end of the tool of FIG. 5.

FIGS. 5–7 show an alternative fill tube 40 having a single side opening 30. As shown, the apex 42 is partially closed and the tube is angled toward the apex 42 to help guide and direct the material within the tube out to the side opening 30.

Tests show a dramatic increase in distraction forces for filling a bag with a tool of the invention in comparison to a fill tool which has an opening in line with its longitudinal axis. Since bone replacement material tends to become quite rigid under pressure, injection of bone replacement material into the bag at an angle relative to the longitudinal axis of the fill tube allows the bag to inflate and create forces which are not directed to eject the fill tool.

If the internal diameter of the tube is D, the length of the side opening 30 is preferably between about 1½ to 3D. If the side opening 30 length is only 1D or smaller, harder pushing is required and packing of the material may result in the tube. The distal end of the tube 40 towards the apex 42 is also preferably angled to direct the flow and to break down any material that has packed back into more discrete pieces. The end adjacent the apex 42 of the tool may be completely closed or open up to ½D which still provides good side direction of product.

Figure 8:
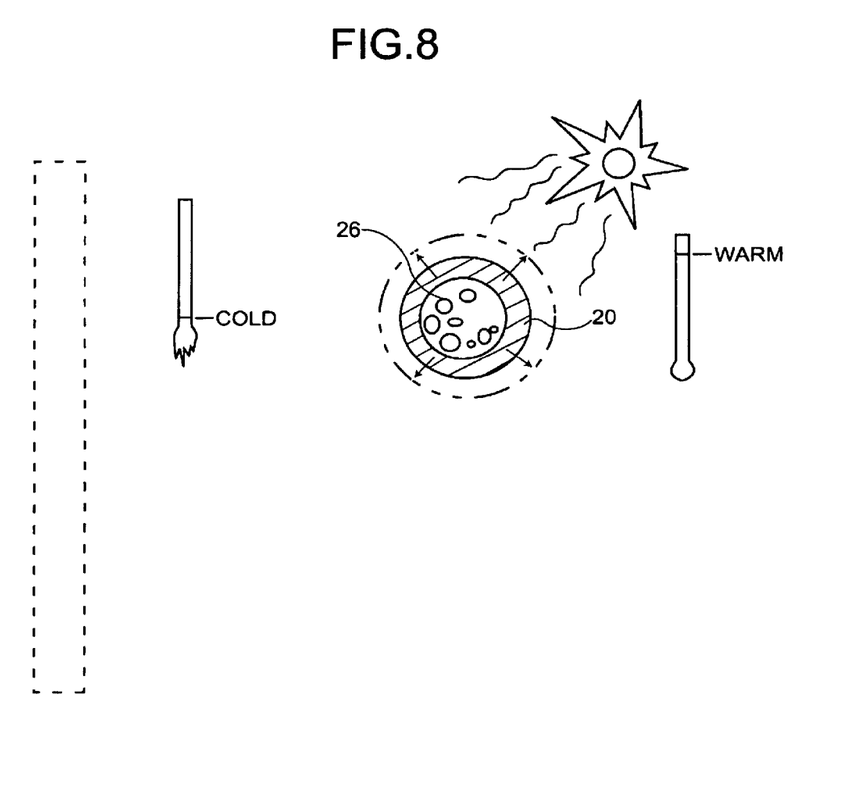
FIG. 8 is a representation of the effects of temperature change on the filled tubes of the invention showing a filled tube in cross-section.

FIG. 8 depicts a filled tube 20, 40 of the invention which has been filled with bone replacement material 26. The invention contemplates cooling the tubes prior to use and warming them just prior to use such that expansion of the metal tube causes expansion to help decrease friction to the tube. In addition, if thawing occurs at the metal interface with the bone replacement material, a liquid layer will be formed to lubricate the replacement material within the tube. This allows easier egress of material within the tube.

Figure 9:
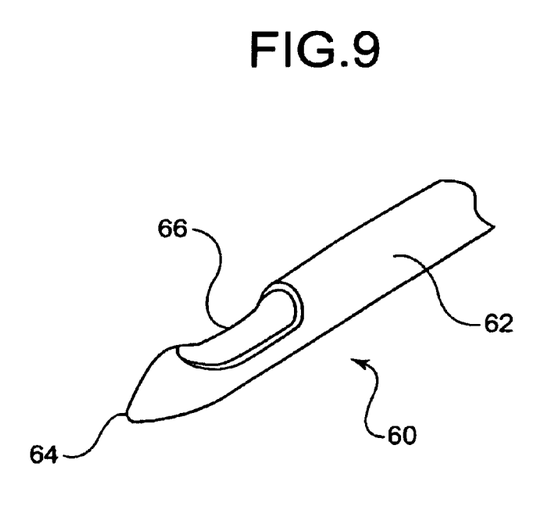
FIG. 9 is a perspective view of a graft insertion tool suitable for use with inserting a band.
Figure 10:
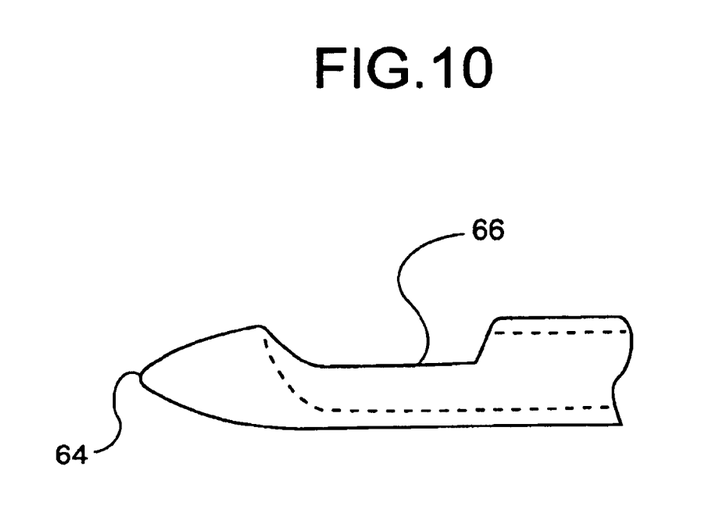
FIG. 10 is a side view of the tool shown in FIG. 9.
Figure 11:
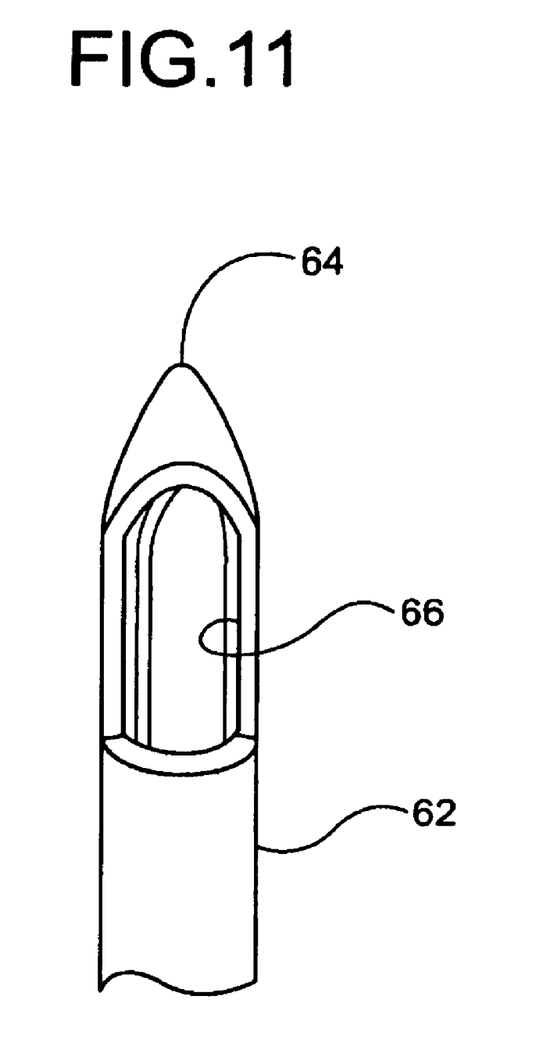
FIG. 11 is a top down view of the tool of FIG. 9.
Figure 12:
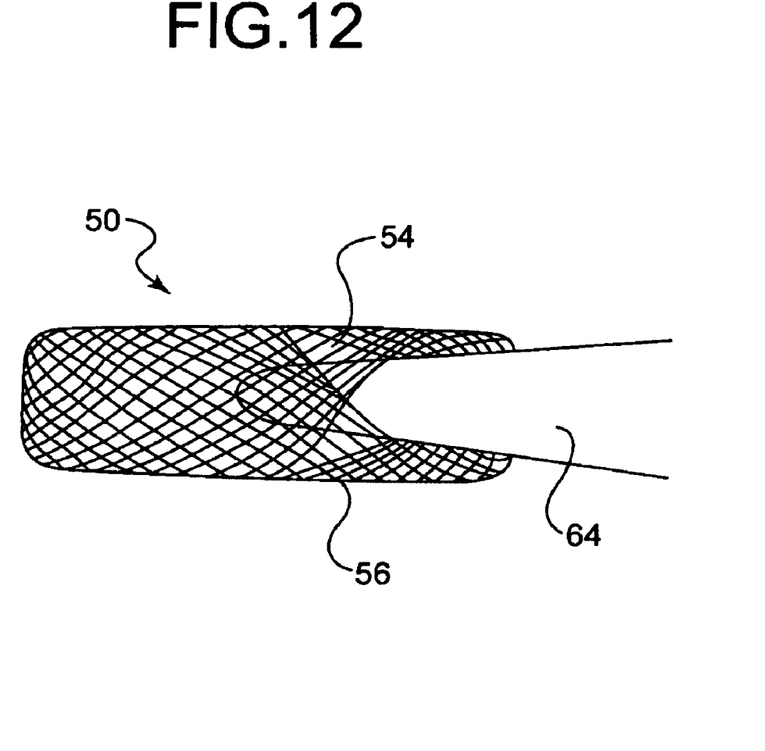
FIG. 12 is a side view of the tool of FIG. 9 seen dislocating the fibers of a band.
Figure 13:
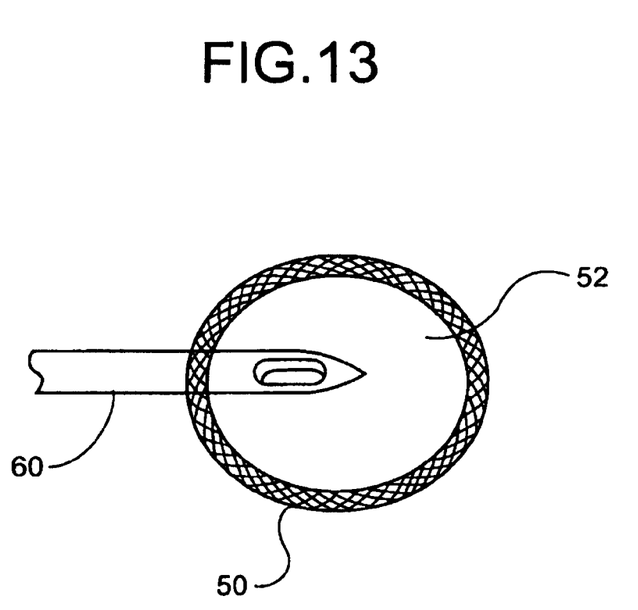
FIG. 13 is a top down cut away view of the tool of FIG. 9 as may be seen during graft insertion.

As may be seen in FIG. 9, the tool may also be used to insert a single walled band into a cavity formed in a spinal disc as disclosed in co-pending U.S. Patent Application entitled Expandable Tube for Spinal Stabilization, to Kuslich, and is filed concurrently herewith. The entire contents of the aforementioned concurrently filed application is incorporated herein by reference. As shown in FIG. 12 and 13, the band 50 is shown with a graft insertion tool 60 being inserted into the interior 52 of the band 50 by passing through one of the spaces or pores 54. The shape of the tool 60 as may best be seen in FIGS. 9–11 is essentially an elongate shaft 62 having a tapered or pointed distal end 64.

The tapered distal end 64 of the tool 60 is sized to enlarge the opening 54 to allow passage of the tool 60 into the interior 52 by pushing aside the various fibers 56 as may best be seen in FIG. 12. The fibers 56 are disposed to open the pore 54 from its nominal diameter of 0.25 to 5 mm to an enlarged opening sufficient to allow passage of a portion of the shaft 62 therethrough The extent of tool penetration into the band interior 52 must be sufficient to allow the side opening 66 to be fully contained within the band interior 52. The tool 60 may include more than one side opening 66.

As shown in FIG. 13, the side opening 66 allows insertion of the bone graft material into the band interior 52. The tool 60 includes a means for pushing graft material from within the shaft 62, through the side opening 66 and into the band interior 52.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated. For example, the inventive device and methods may be used whenever replacement material needs to be directed into a defined location and not just when a bag is to be filled within a disc cavity.

This completes the description of the preferred and alternate embodiments of the invention. Those skilled in the art may recognize other equivalents to the specific embodiment described herein which equivalents are intended to be encompassed by the claims attached hereto.

What is claimed is:

1. A system for filling a bone cavity comprising:
   a fill container, the fill container comprising a wall the wall defining a fill apace;
   a predetermined quantity of bone replacement material; and
   a tool for directing the bone replacement material into the fill space, the tool comprising:
   a) an elongated hollow tube having a proximal and a distal end, said proximal end being adapted for attachment to a source of the bone replacement material wider pressure; and
   b) said distal end including at least one deflector opening for deflecting the bone replacement material out of said tube and into the fill space at an angle relative to a longitudinal axis of said tube, each said at least one deflector opening having a length of between about 1 D to 3 D, wherein D is the internal diameter of said tube, the distal end comprising a tip, the tip having a tapered shape.

2. The system of claim 1 wherein each said deflector opening includes a deflector for deflecting bone replacement material from said tube through said deflector opening.

3. The system of claim 2 including two opposing deflector openings and said deflector is a tapered wedge adjacent the distal end of said tube.

4. The system of claim 2 including a single deflector opening and said deflector presents an angled ramp to said deflector opening.

5. The system of claim 4 wherein said distal end of said tube is closed or open up to 2 D.

6. The system of claim 1 where in the wall of the fill container defines a plurality of openings, the plurality of openings being sufficiently small so as to prevent the bone replacement material from passing therethrough.

7. The system of claim 6 wherein each of the plurality of openings has a nominal diameter of about 0.25 mm to about 5 mm.

8. The system of claim 6 wherein at least one of the plurality of openings is expandable from the nominal diameter to an enlarged diameter, the enlarged diameter being at least as large as outer diameter of the tube.

9. The system of claim 1 wherein the fill container comprises a mesh bag, the mesh bag having a plurality of openings therethrough, the plurality of openings sized to retain the bone replacement material within the fill opening.

10. The system of claim 9 wherein the at least the distal end of the tube and at least one of the plurality of openings are of a complementary size to allow at least a portion of the distal end of the tube to pass through the at least one of the plurality of openings.

11. A method of filling a bone cavity utilizing the system of claim 1 comprising the steps of:
   inserting the fill container into a bone cavity;
   filling at least a portion of the tube with the bone replacement material;
   inserting at least a portion of the distal end of the tube into the fill space;
   injecting the bone replacement material out of the at least one deflector opening and into the fill space at the angle relative to the longitudinal axis of said tube; and
   withdrawing the tube from the fill container.

12. A tool for directing bone replacement material into a defined space comprising:
   a) an elongated hollow tube having a proximal and a distal end, said proximal end being adapted for attachment to a source of bone replacement material under pressure; and
   b) said distal end including at least one deflector opening for deflecting bone replacement material out of said tube at an angle relative to a longitudinal axis of said tube, each said at least one deflector opening having a length of between about 1 D to 3 D, wherein D is the internal diameter of said tube.

13. The system of claim 12 wherein each said deflector opening includes a deflector for deflecting bone replacement material from said tube through said deflector opening.

14. The system of claim 13 including two opposing deflector openings and said deflector is a tapered wedge adjacent the distal end of said tube.

15. The system of claim 13 including a single deflector opening and said deflector presents an angled ramp to said deflector opening.

16. The system of claim 15 wherein said distal end of said tube is closed or open up to 2 D.

* * * * *